United States Patent
Wang et al.

(10) Patent No.: US 8,481,129 B2
(45) Date of Patent: Jul. 9, 2013

(54) LIQUID CRYSTAL COMPOUNDS, AND LIQUID CRYSTAL DISPLAYS AND PHOTOCHROMIC MATERIALS COMPRISING THE LIQUID CRYSTAL COMPOUNDS

(75) Inventors: Yi-Rong Wang, Taipei (TW); Chih-Lung Chin, Longtan Township, Taoyuan County (TW); Wan-Chi Chen, Sinwu Township, Taoyuan County (TW); Kung-Lung Cheng, Hsinchu (TW); Shih-Hsien Liu, Jhubei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/340,206

(22) Filed: Dec. 29, 2011

(65) Prior Publication Data

US 2013/0135574 A1   May 30, 2013

(30) Foreign Application Priority Data

Nov. 25, 2011   (TW) .............................. 100143258 A

(51) Int. Cl.
*C09K 19/32* (2006.01)
*C09K 19/30* (2006.01)
*C09K 19/34* (2006.01)
*C09K 19/20* (2006.01)
*C07C 69/78* (2006.01)
*C07D 307/04* (2006.01)

(52) U.S. Cl.
USPC .................. 428/1.1; 252/299.61; 252/299.62; 252/299.63; 252/299.67; 560/80; 560/256; 549/429

(58) Field of Classification Search
CPC ............................ C09K 2019/327; C09K 19/32
USPC ........... 428/1.1; 252/299.01, 299.61, 299.62, 252/299.63, 299.67; 560/80, 256; 568/731, 568/734; 549/429
See application file for complete search history.

(56) References Cited

U.S. PATENT DOCUMENTS

| | | | |
|---|---|---|---|
| 5,883,218 A | 3/1999 | Gordon et al. | |
| 6,288,206 B1 | 9/2001 | Stewart et al. | |
| 6,589,445 B2 | 7/2003 | Sugiyama et al. | |
| 6,610,216 B2 | 8/2003 | Yumoto et al. | |
| 7,122,227 B2 | 10/2006 | Vaughn-Spickers et al. | |
| 7,214,834 B2 | 5/2007 | Welter | |
| 7,294,369 B2 | 11/2007 | Harding et al. | |
| 7,329,368 B2 | 2/2008 | Welter | |
| 7,452,482 B2 | 11/2008 | Welter | |
| 7,470,376 B2 | 12/2008 | Welter et al. | |
| 7,635,525 B2 | 12/2009 | Iwanaga | |
| 2002/0076510 A1 | 6/2002 | Farrand | |

FOREIGN PATENT DOCUMENTS

WO   WO 2004/087835 A1   10/2004

OTHER PUBLICATIONS

Caccamese et al., "Chiral HPLC separation and CD spectra of the enantiomers of a molecular 'hamburger'", Mendeleev Communications, vol. 14, No. 6, 2004, pp. 237-239.

Köhler et al., "Novel chiral macrocycles containing two electronically interacting arylene chromophores", Chemical European Journal, 2001, vol. 7, No. 14, pp. 3000-3004.

Sen et al., "Spiro-biindane containing fluorinated poly(ether imide)s: synthesis; characterization and gas separation properties", Journal of Membrane Science, vol. 365, 2010, pp. 329-340.

Stenzel et al., "Bis(2,4,7-trimethylindenyl)cobalt(II) and rac-2,2',4,4',7,7'-hexamethyl-1,1'-biindene", Acta Crystallographica Section C, Sep. 2001; C57, pp. 1056-1059.

*Primary Examiner* — Shean C Wu
(74) *Attorney, Agent, or Firm* — Birch, Stewart, Kolasch & Birch, LLP

(57) ABSTRACT

A liquid crystal compound of Formula (I) is provided.

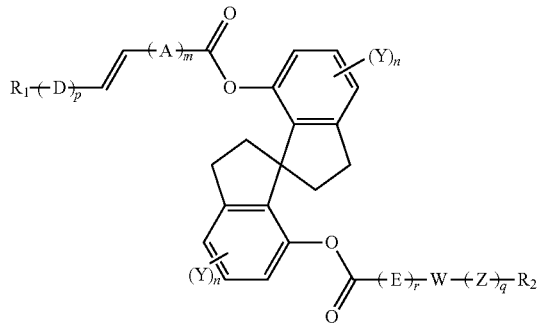

In Formula (I), A is benzene, naphthalene, pyridine, furan, thiophene or a single bond, D is benzene, naphthalene, pyridine, furan, thiophene or a single bond, $R_1$ and $R_2$ are C1-10 alkyl, C1-10 alkoxy, fluoro or trifluoro methyl, E is benzene, naphthalene, pyridine, furan, thiophene or a single bond, W is —CO—O—, —O—CO—, —O—, —$CH_2$—$CH_2$—, —CH=CH—, —$CH_2$—O— or a single bond, Z is benzene, naphthalene, pyridine, furan, thiophene or a single bond, Y is hydrogen, methyl, ethyl or propyl, m is 0, 1 or 2, p is 0, 1 or 2, r is 0, 1 or 2, q is 0, 1 or 2, and n is 0, 1, 2 or 3. The invention also provides a liquid crystal display and photochromic material including the compound.

5 Claims, No Drawings

LIQUID CRYSTAL COMPOUNDS, AND LIQUID CRYSTAL DISPLAYS AND PHOTOCHROMIC MATERIALS COMPRISING THE LIQUID CRYSTAL COMPOUNDS

CROSS REFERENCE TO RELATED APPLICATIONS

This Application claims priority of Taiwan Patent Application No. 100143258, filed on Nov. 25, 2011, the entirety of which is incorporated by reference herein.

BACKGROUND OF THE INVENTION

1. Field of the Invention

The invention relates to a liquid crystal compound, and more particularly to a liquid crystal compound with high color stability and a liquid crystal display comprising the compound.

2. Description of the Related Art

A reflective flexible display is the most important type of electronic display for next generation. The reflective flexible display utilizes plastic as a substrate material to replace traditional glass substrates, and has characteristics of being light, thin, and rugged etc. and may be made as roll-up displays for application as, for example, electronic tags, e-books, smart cards, flat panel displays, large billboards and tablet PCs etc.

A cholesteric phase can display various colors due to the selective reflection properties. In addition, its characteristic of bistability in a device can also make a screen "stay" like the display of a painting or a book without being applied voltage and can drive the cholesteric phase using voltage when switching of the screen is needed. This operation dramatically saves power consumption of a display and makes it much easier to carry and read. It is also one of the important trends for development of e-books.

In order to manufacture light-writing cholesteric liquid crystal displays, light-responsive chiral compounds having high helical twisting power (HTP) are needed. The molecular conformation of such compounds in liquid crystal is altered by illumination, resulting in an alteration of HTP and pitches of the cholesteric liquid crystals, which achieves an effect of changing colors of reflected light. Synthesis of a chiral dopant having a higher HTP value is desirable. When the chiral dopant is added to liquid crystals, the performance of the liquid crystals will not be lower and only a small amount thereof is needed to achieve the same twisting effect. Also, the problem of solubility will not be caused. A colorless light-responsive chiral compound is also required. Otherwise, a color light-responsive chiral compound will interfere with the wavelength of reflected light.

Therefore, when adding to liquid crystal formulation, light-responsive chiral compounds having the characteristics of a high HTP value, good solubility with liquid crystal formulation and being colorless etc. are required.

BRIEF SUMMARY OF THE INVENTION

One embodiment of the invention provides a liquid crystal compound of Formula (I).

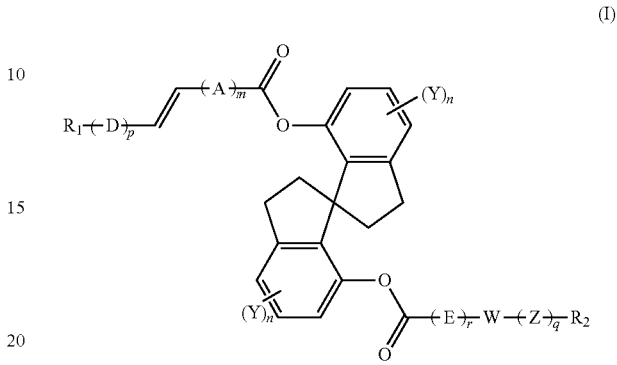

(I)

In Formula (I), A is benzene, naphthalene, pyridine, furan, thiophene or a single bond; D is benzene, naphthalene, pyridine, furan, thiophene or a single bond; $R_1$ and $R_2$ are C1-10 alkyl, C1-10 alkoxy, fluoro or trifluoro methyl; E is benzene, naphthalene, pyridine, furan, thiophene or a single bond; W is —CO—O—, —O—CO—, —O—, —$CH_2$—$CH_2$—, —CH=CH—, —$CH_2$—O— or a single bond; Z is benzene, naphthalene, pyridine, furan, thiophene or a single bond; Y is hydrogen, methyl, ethyl or propyl; m is 0, 1 or 2; p is 0, 1 or 2; r is 0, 1 or 2; q is 0, 1 or 2; and n is 0, 1, 2 or 3.

One embodiment of the invention provides a liquid crystal display, comprising: an upper substrate; a lower substrate opposed to the upper substrate; and a liquid crystal layer disposed between the upper substrate and the lower substrate, wherein the liquid crystal layer comprises the liquid crystal compound of Formula (I).

One embodiment of the invention provides a photochromic material, comprising: a substrate; and a micro-cell liquid crystal layer coated on the substrate, wherein the micro-cell liquid crystal layer comprises the liquid crystal compound of Formula (I).

The invention discloses a novel light-responsive chiral compound having the characteristics of a high HTP value, good solubility with liquid crystal formulation, stable temperature dependence, minor alteration in wavelength when illumination time is increased, precise control to color wavelengths of cholesteric liquid crystals and improvement in stability of cholesteric liquid crystals under the surrounding environment etc.

A detailed description is given in the following embodiments.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides a liquid crystal compound of Formula (I).

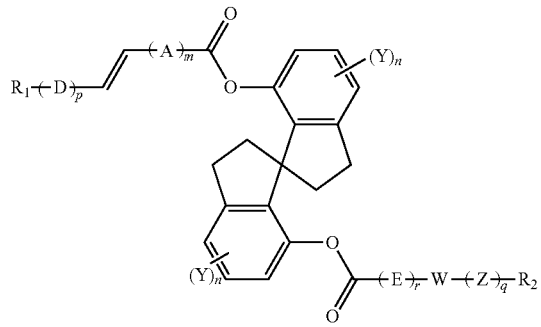

(I)

In Formula (I), A may comprise benzene, naphthalene, pyridine, furan, thiophene or a single bond.

D may comprise benzene, naphthalene, pyridine, furan, thiophene or a single bond.

$R_1$ and $R_2$ may comprise C1-10 alkyl, C1-10 alkoxy, fluoro or trifluoro methyl.

E may comprise benzene, naphthalene, pyridine, furan, thiophene or a single bond.

W may comprise —CO—O—, —O—CO—, —O—, —CH=CH—, —CH$_2$—O— or a single bond.

Z may comprise benzene, naphthalene, pyridine, furan, thiophene or a single bond.

Y may comprise hydrogen, methyl, ethyl or propyl. In an embodiment, Y may comprise —F, —Cl, —Br, —CN or —OR(R may comprise methyl, ethyl or propyl).

m may be 0, 1 or 2.

p may be 0, 1 or 2.

r may be 0, 1 or 2.

q may be 0, 1 or 2.

n may be 0, 1, 2 or 3.

Specific liquid crystal compounds in other embodiments of the invention are disclosed as follows.

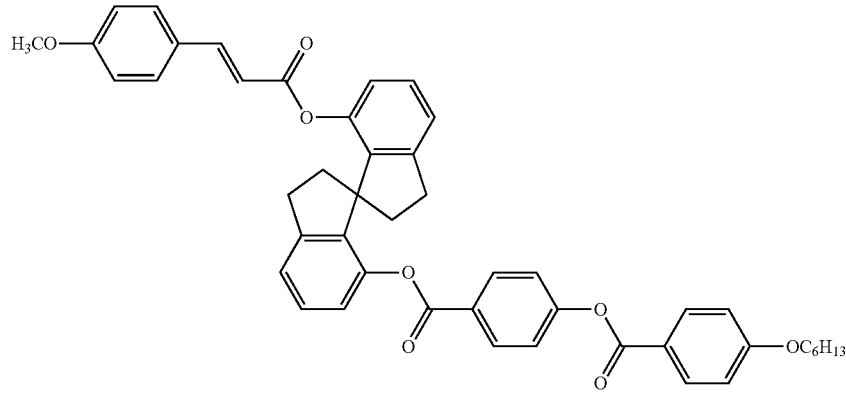

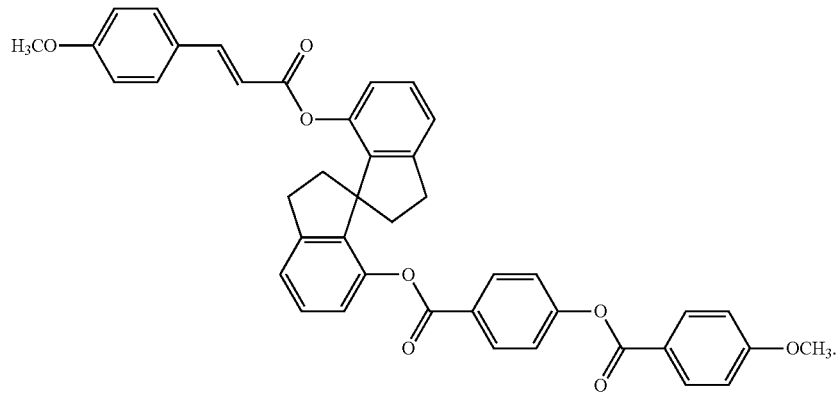

One embodiment of the invention provides a liquid crystal display comprising an upper substrate, a lower substrate opposed to the upper substrate, and a liquid crystal layer disposed between the upper substrate and the lower substrate. The liquid crystal layer comprises the liquid crystal compound of Formula (I).

The upper and lower substrates may be a color filter substrate, an array substrate, an array on color filter substrate (AOC), a color filter on array substrate (COA) or a transparent substrate such as a glass substrate or a plastic substrate.

One embodiment of the invention provides a photochromic material comprising a substrate, and a micro-cell liquid crystal layer coated on the substrate. The micro-cell liquid crystal layer comprises the liquid crystal compound of Formula (I).

The substrate may be a color filter substrate, an array substrate, an array on color filter substrate (AOC), a color filter on array substrate (COA) or a transparent substrate such as a glass substrate or a plastic substrate.

The invention discloses a novel light-responsive chiral compound having the characteristics of a high HTP value, good solubility with liquid crystal formulation, stable temperature dependence, minor alteration in wavelength when illumination time is increased, precise control to color wavelengths of cholesteric liquid crystals and improvement in stability of cholesteric liquid crystals under the surrounding environment etc.

Example 1

Preparation of the Liquid Crystal Compound I

Under room temperature, 42.08 g of KOH (700 mmol) was dissolved in 180 mL of ethanol to form a solution. The solution was cooled to 5° C. under an ice bath. 73.2 g of 3-hydroxybenzaldehyde (600 mmol) was slowly added to the solution to form a yellow sludge. During this step, the temperature of the solution was slightly increased. After the yellow sludge was cooled, 22.05 mL of acetone (300 mmol) was added thereto dropwisely through a funnel under an ice bath with stirring for about 30 minutes to form a solution (the temperature was risen and then fallen). After removal of the ice bath, the solution was stirred for about 4.5 hours under room temperature to form a red solution. The formed red solution was poured into 300 mL of an ice water. 45 mL of acetic acid was then added to the ice water to neutralize the reaction. The red solution was converted into a bright yellow sludge. After string for about 15 minutes, the sludge was poured into a flask and stood for 10 minutes. The lower-layered bright yellow sludge was collected, cooled to 5° C. and filtered. A filtrate was washed with plenty of water and a small amount of ethanol/water (1:2(v/v)) solution. A solid product was then washed with a small amount of water and dried under air. 48.06 g of a bright yellow solid (180 mmol) was obtained, with 80% yield.

I

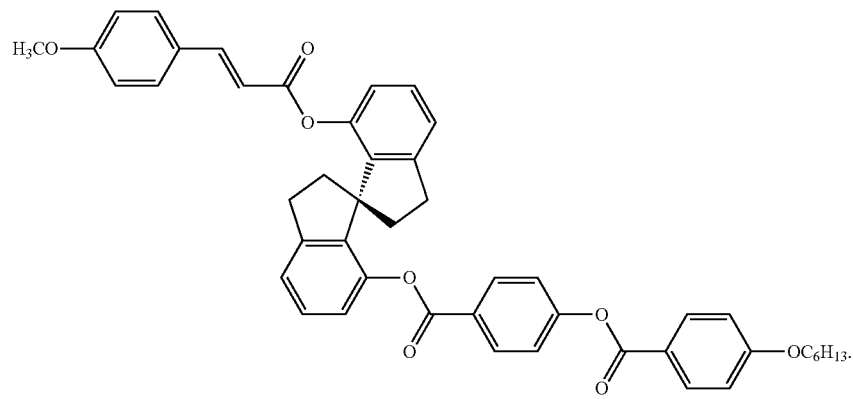

Step I-1:
Synthesis Scheme:

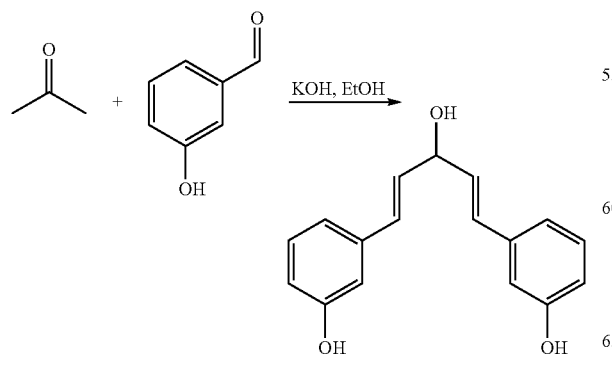

Step I-2:
Synthesis Scheme:

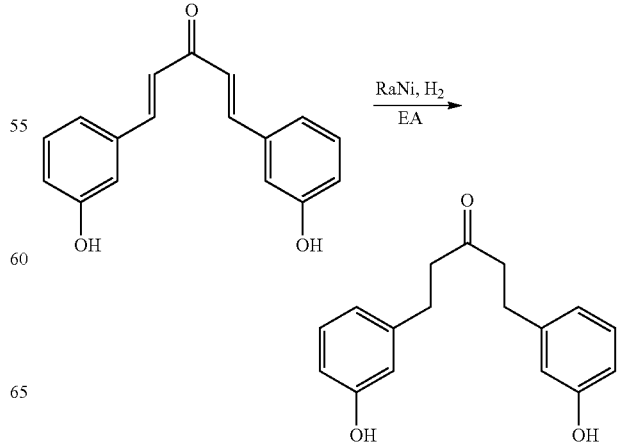

5.00 g of the product (18.791 mmol) obtained from step I-1 was dissolved in 18.8 mL of ethyl acrylate (EA) in a reaction flask. 0.15 g of a catalyst (RaNi) was washed with THF for three times (to remove the solvent on RaNi surface) and added to the reaction flask. After removal of air in the reaction flask through a vacuum system, a hydrogen reaction was performed using a hydrogen balloon under room temperature. Initially, the reaction was slightly exothermic. After about 10 hours, the reaction temperature was dropped by to room temperature. A TLC film (SiO$_2$) was used to confirm the completion of the reaction. A product was carefully filtered using celite. The used filter bottle was washed with a small amount of ethyl acrylate (EA). After a filtrate was dried using a low-pressure condenser, 4.81 g of thick liquid (17.79 mmol) was obtained, with about 95% yield.

Step 1-3:
Synthesis Scheme:

Step 1-4:
Synthesis Scheme:

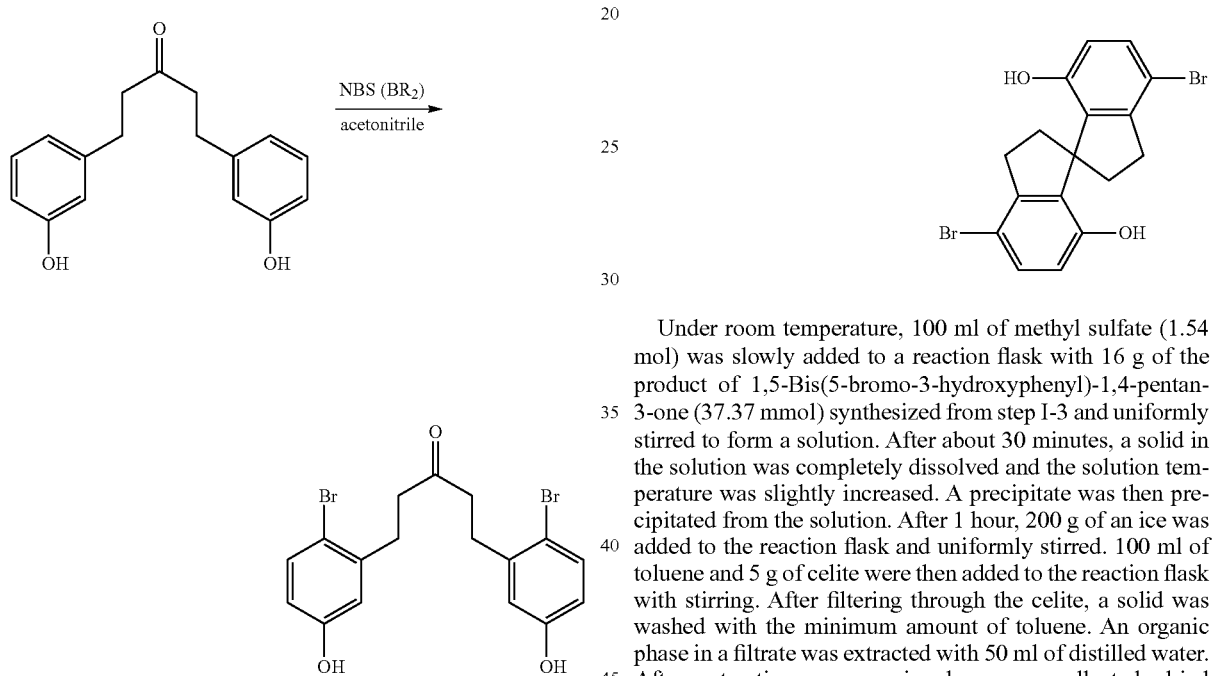

Under an ice bath, 29.35 g of the product (108.6 mmol) obtained from step 1-2 was dissolved in 108 mL of acetonitrile, and 1.2 mL of Br$_2$ (24 mmol) was then added thereto to form a solution. 38.74 g of N-bromosuccinimide (NBS) (217.4 mmol) was added to the solution four times. The temperature of the solution was arisen about 12° C. for each time NBS was added. NBS was added for a next time only when the temperate was dropped by 5° C. The time for the four times for which the NBS was added was more than 30 minutes. After the last time the NBS was added, the solution was stirred for 1 hour under an ice bath and then stirred for an additional 1 hour when the temperature returned to room temperature. HPLC (ethyl acrylate:hexane=1:1) was used to confirm the completion of the reaction. The solution was dried using a low-pressure condenser to form a mixture of a product and by-products (succinimide-like compounds). The mixture was then stirred for about 1 hour at 55° C. in 300 mL of water to remove the by-products. After suction filtration, a solid product was washed with a small amount of water. Next, the solid product was stood to dry in air. 43.25 g of a skin-colored product (101 mmol) was obtained, with 93% yield.

Under room temperature, 100 ml of methyl sulfate (1.54 mol) was slowly added to a reaction flask with 16 g of the product of 1,5-Bis(5-bromo-3-hydroxyphenyl)-1,4-pentan-3-one (37.37 mmol) synthesized from step I-3 and uniformly stirred to form a solution. After about 30 minutes, a solid in the solution was completely dissolved and the solution temperature was slightly increased. A precipitate was then precipitated from the solution. After 1 hour, 200 g of an ice was added to the reaction flask and uniformly stirred. 100 ml of toluene and 5 g of celite were then added to the reaction flask with stirring. After filtering through the celite, a solid was washed with the minimum amount of toluene. An organic phase in a filtrate was extracted with 50 ml of distilled water. After extraction, an organic phase was collected, dried through sodium sulfate and filtered. After removal of solvent through low-pressure concentration, a first product was dissolved in 30 ml of diisopropylether (IPE), and 120 ml of n-heptane was added thereto and violently stirred to form a sludge. After stirring for 30 minutes, impurities were filtered out. An organic phase in a filtrate was then dried and concentrated. 11.71 g of the product (28.55 mmol) was obtained, with 76% yield.

Step 1-5:
Synthesis Scheme:

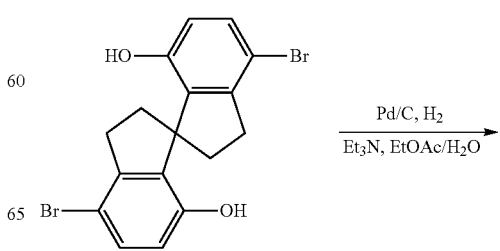

-continued

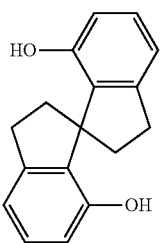

11.71 g of dibromospirobiindane (28.55 mmol) synthesized from step I-4 was placed in a reaction flask. 80 mL of ethyl acetate (EA), 23 mL of distilled water, 80 mL of $Et_3N$ (0.58 mol) and 1.16 g of a catalyst (Pd/C) (10% Pd/C) were added to the reaction flask. A reaction was performed using a hydrogen balloon. The reaction was slightly exothermic. HPLC was used to confirm the completion of the reaction. A mixture product was filtered through celite. An organic phase in a filtrate was washed with 10 mL of an HCl aqueous solution (5%). After washing, an organic phase was collected, dried through sodium sulfate and filtered. After removal of solvent by low-pressure condensation, a column chromatography was performed using an eluting solvent (ethyl acrylate:hexane=1:1). A white solid product was obtained, with 65% yield.

Step 1-6:
Synthesis Scheme:

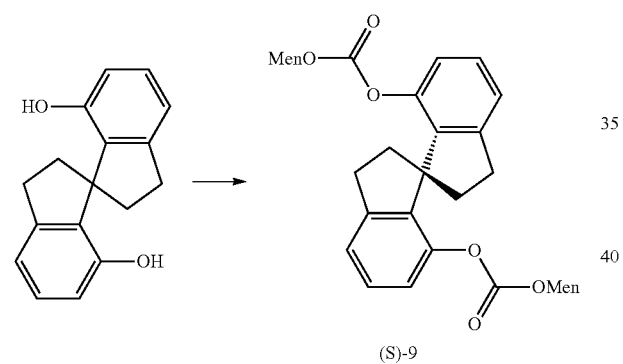

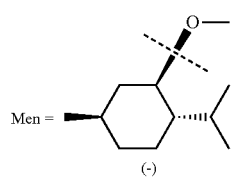

0.5 g of the product (racemic diol) (1.98 mmol) obtained from step I-5 was dissolved in 5 mL of ethyl acetate (EA) to form a solution. 0.7 mL of $Et_3N$ (4.9 mmol) and 0.024 g of DMAP (0.19 mmol) were added to the solution under an ice bath (the solution temperature was lower than 5° C.). 0.9 mL of (−)-methyl chloroformate (4.16 mmol) was slowly dropped into the solution within 15 minutes. During this step, the solution was slightly exothermic, the temperature thereof was increased to about 15° C. and a white precipitate was formed. After 30 minutes, 3 mL of an HCl aqueous solution (5%) were added to the solution under an ice bath to form a mixture. The mixture was filtered to obtain a small amount of a solid product. The solid product was dissolved in 1.50 mL of THF to form a solution. An organic phase in a filtrate was collected and incorporated into the solution. The solution was dried through magnesium sulfate and filtered. After removal of solvent from a filtrate by low-pressure condensation, 2.50 mL of n-heptane was added thereto, stirred for 30 minutes under an acetone/ice bath and filtered. The solid was washed with the minimum amount of an ice n-heptane and dried in air. A colorless solid product (bis-carbonate) ((S)-9) was obtained, with 40% yield.

Step I-7:
Synthesis Scheme:

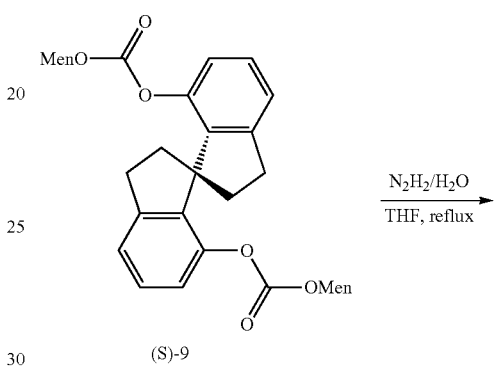

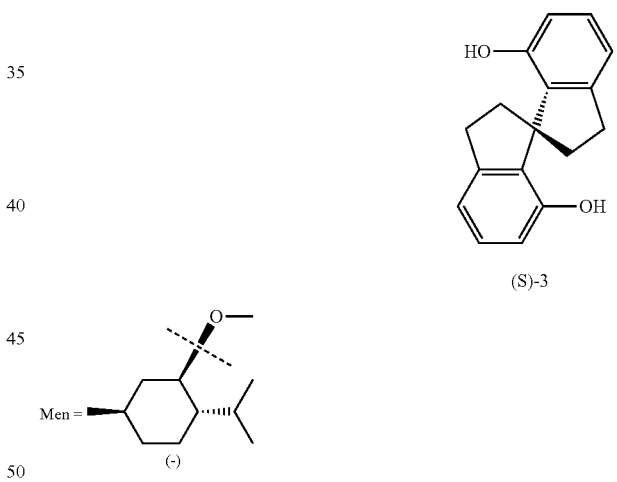

41.1 g of the product (bis-carbonate) ((S)-9) (66.6 mmol) obtained from step I-6 was dissolved in 50 mL of THF in a reaction flask. 16 mL of hydrazine hydrate (333 mmol) was added to the reaction flask with thermal reflux for 80 minutes. 250 mL of an ice NaOH aqueous solution (5%) was added to the reaction flask to form a mixture. The mixture was extracted using 200 mL of diisopropyl ether. A first water phase was kept. A first organic phase was extracted using 100 mL of an NaOH aqueous solution (5%). A second water phase was collected. The first and second water phases were mixed to form a solution and 65 mL of conc. HCl (pH≦2) was carefully added thereto. A precipitate was thus formed. The solution was cooled to below 5° C. through an ice bath and filtered. The solid was collected, washed with a small amount of water and dried in air. A colorless solid product (diol) ((S)-3) was obtained, with 87% yield.

Step 1-8:
Synthesis Scheme:

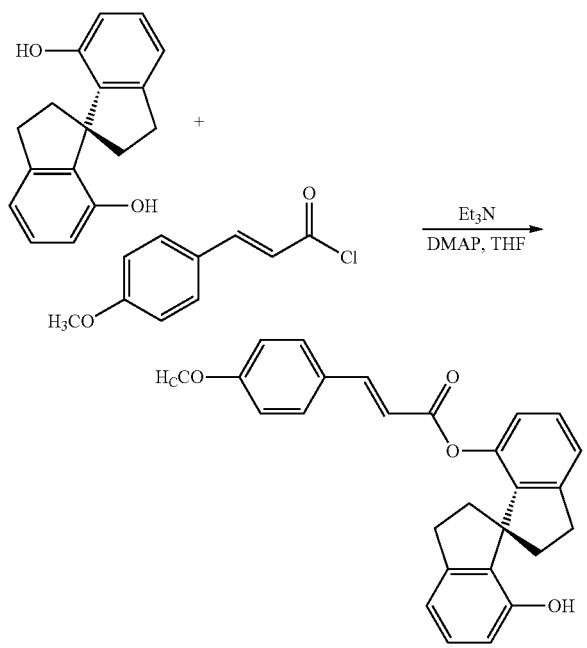

1 g of the product (chiral diol) ((S)-3) (3.96 mmol) obtained from step I-7 was dissolved in 10 mL of THF to form a solution. 1.4 mL of Et$_3$N (10.04 mmol) and 0.05 g of DMAP (0.4 mmol) were added to the solution under an ice bath (the solution temperature was lower than 5° C.). 0.77 g of acyl chloride (3.96 mmol) was slowly added to the solution. During this step, the solution was slightly exothermic and a white precipitate was formed. After the solution temperature returned to room temperature, the solution was stirred for about 1 hour. 20 mL of an HCl aqueous solution (5%) was added to the solution under an ice bath. The solution was extracted using 20 ml of ethyl acetate. An organic phase was collected, dried through sodium sulfate and filtered. After removal of solvent from a filtrate by low-pressure condensation, a column chromatography was performed using n-hexane and ethyl acetate (EA) as an eluting solution. A white solid was obtained, with 65% yield.

Step I-9:
Synthesis Scheme:

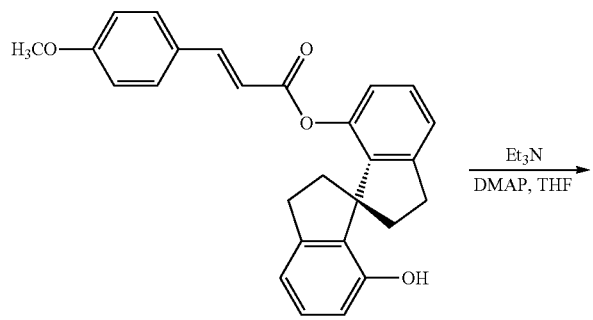

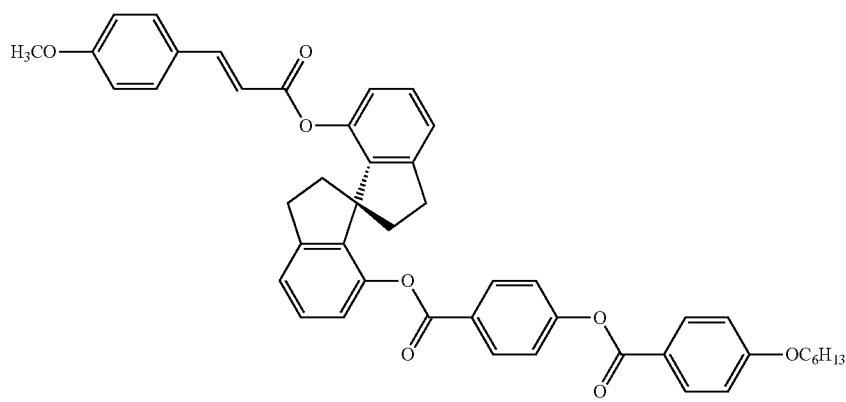

1 g of the product (2.4 mmol) obtained from step I-8 was dissolved in 20 mL of THF to form a solution. 0.84 mL of Et₃N (6.02 mmol) and 0.03 g of DMAP (0.24 mmol) were added to the solution under an ice bath (the solution temperature was lower than 5° C.). 1.29 g of acyl chloride (3.6 mmol) was slowly added to the solution. During this step, the solution was slightly exothermic and a white precipitate was formed. After the solution temperature returned to room temperature, the solution was stirred for about 1 hour. 20 mL of an HCl aqueous solution (5%) was added to the solution under an ice bath. The solution was extracted using 20 ml of ethyl acetate. An organic phase was collected, dried through sodium sulfate and filtered. After removal of solvent from a filtrate by low-pressure condensation, a column chromatography was performed using n-hexane and ethyl acetate as an eluting solution. A white solid was obtained, with 79% yield.

Example 2

Preparation of the Liquid Crystal Compound II

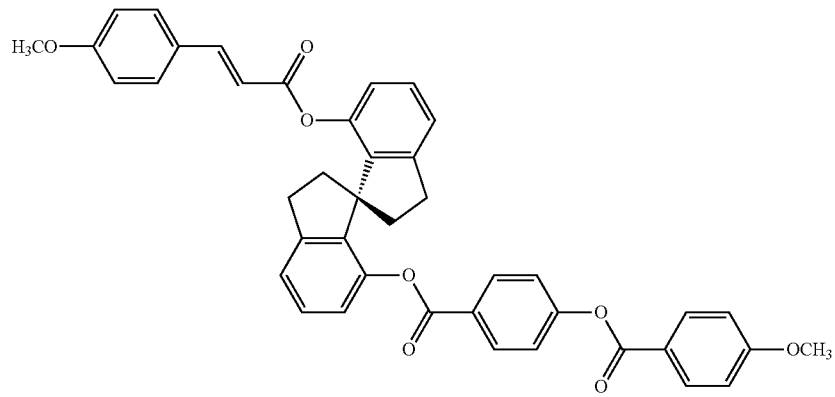

Step II-1:
Synthesis Scheme:

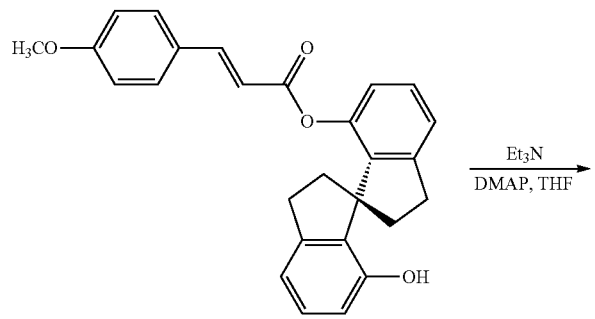

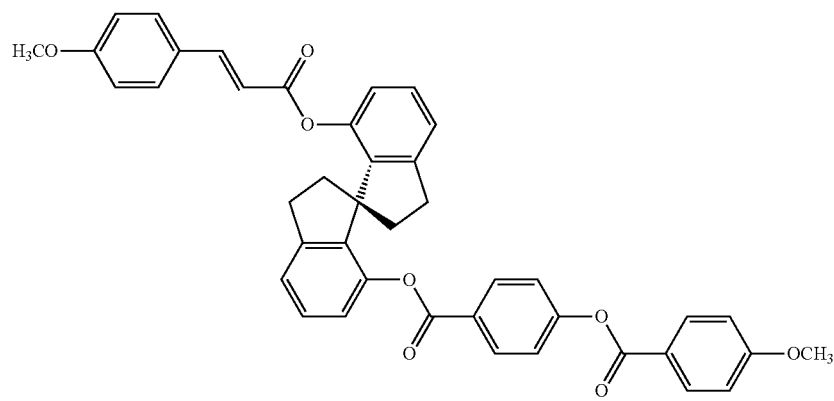

1 g of the product (2.42 mmol) obtained from step I-8 was dissolved in 20 mL of THF to form a solution. 0.84 mL of Et$_3$N (6.02 mmol) and 0.03 g of DMAP (0.24 mmol) were added to the solution under an ice bath (the solution temperature was lower than 5° C.). 0.53 g of acyl chloride (3.6 mmol) was slowly added to the solution. During this step, the solution was slightly exothermic and a white precipitate was formed. After the solution temperature returned to room temperature, the solution was stirred for about 1 hour. 20 mL of an HCl aqueous solution (5%) was added to the solution under an ice bath. The solution was extracted using 20 ml of ethyl acetate. An organic phase was collected, dried through sodium sulfate and filtered. After removal of solvent from a filtrate by low-pressure condensation, a column chromatography was performed using n-hexane and ethyl acetate as an eluting solution. A white solid was obtained, with 56% yield.

Example 3

Preparation of the Liquid Crystal Compound III (2)
Synthesis Scheme:

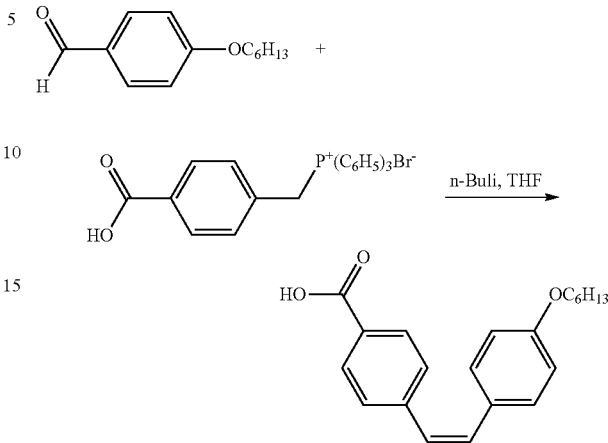

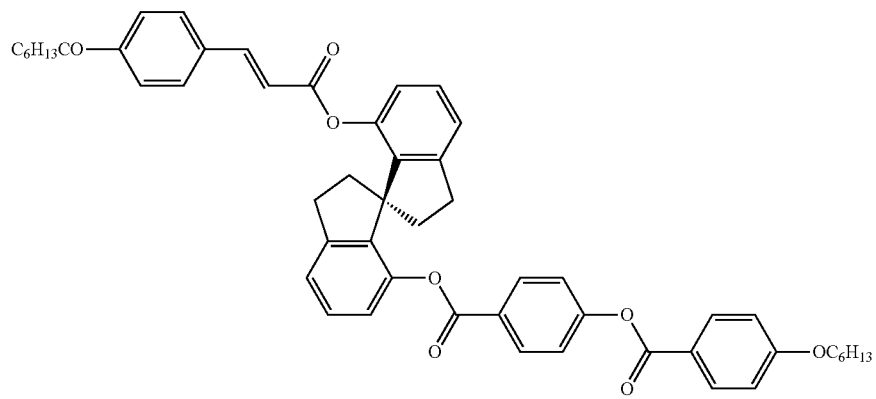

Step III-1:
(1)
Synthesis Scheme:

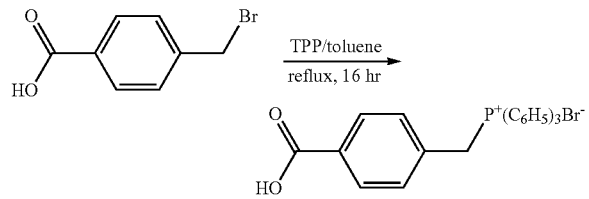

1 g of 4-(bromomethyl)benzoic acid (4.65 mmol) and 1.46 g of triphenylphosphine (TPP) (5.57 mmol) were placed in a single-neck round-bottom flask. Next, 10 ml of toluene was added to the flask to form a solution. A condensing unit was set up. The solution was heated at 110° C. with reflux for 16 hours. After the reaction was completed, a product was washed with hexane and filtered. A white solid was thus obtained.

3 g of the product (6.28 mmol) obtained from the previous step was placed in a two-neck round-bottom flask. After the flask was vacuumed, nitrogen gas and THF were conducted thereinto. Under −78° C., 5 ml of n-BuLi (2.5M) was slowly dropped to the flask and stirred for about 1 hour. 1.2 g of 4-(hexyloxy)benzaldehyde (5.8 mmol) was slowly added to the flask under an ice bath to form a solution. Under 0° C., the solution was stirred for 30 minutes. Under room temperature, the solution was stirred for 16 hours. NMR was used to confirm the completion of the reaction. The solution was extracted using ethyl acetate and concentrated. A light green solid was obtained. The solid was then purified by column chromatography using ethyl acetate and n-hexane as an eluting solution. A white solid was obtained, with 50% yield.

(3) Synthesis Scheme:

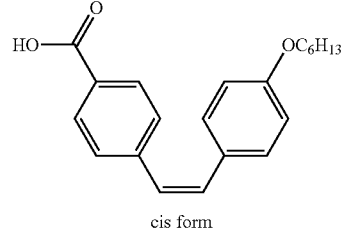

cis form

→ I₂, toluene, reflux →

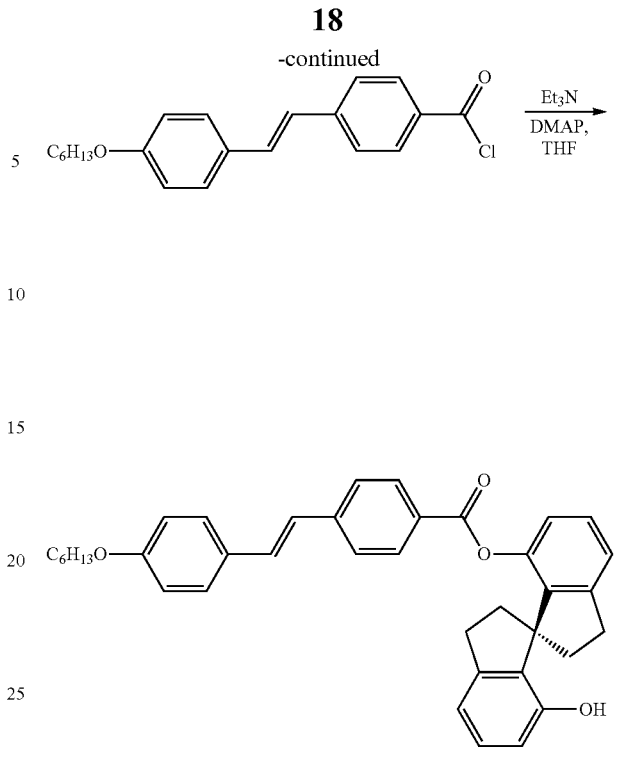

trans form 1.26 g of the white solid (3.67 mmol) obtained from the previous step was placed in a round-bottom flask. 52 ml of toluene and 52 mg of iodine (I₂) were then added to the flask with thermal reflux overnight to form a solution. A white solid was thus precipitated from the solution. The solution was then filtered. After filtering, an iodine color of a solid was washed out using toluene. After vacuum exhaust, a product was weighted, with 87% yield.

(4) Synthesis Scheme:

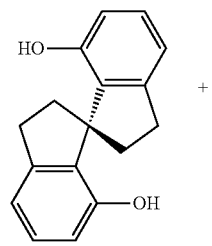

+

1 g of the product (chiral diol) ((S)-3) (3.96 mmol) obtained from step I-7 was dissolved in 10 mL of THF to form a solution. 1.4 mL of Et₃N (10.04 mmol) and 0.05 g of DMAP (0.4 mmol) were added to the solution under an ice bath (the solution temperature was lower than 5° C.). 1.37 g of acyl chloride (3.96 mmol) was slowly added to the solution. During this step, the solution was slightly exothermic and a white precipitate was formed. After the solution temperature returned to room temperature, the solution was stirred for about 1 hour. 20 mL of an HCl aqueous solution (5%) was added to the solution under an ice bath. The solution was extracted using 20 ml of ethyl acetate. An organic phase was collected, dried through sodium sulfate and filtered. After removal of solvent from a filtrate by low-pressure condensation, a column chromatography was performed using n-hexane and ethyl acetate (EA) as an eluting solution. A white solid was obtained, with 60% yield.

Step III-2:
Synthesis Scheme:

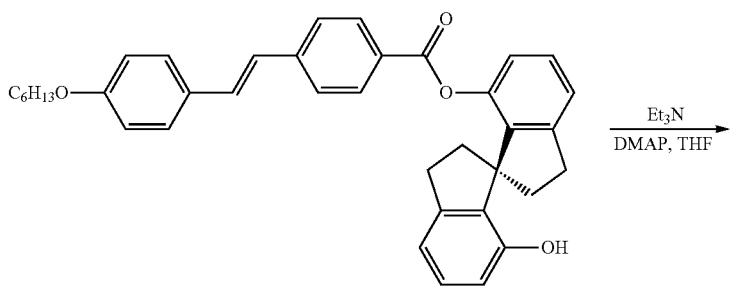

-continued

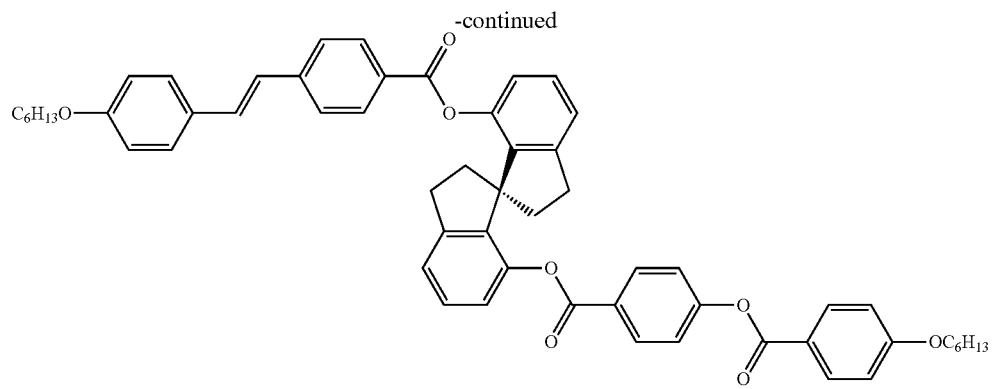

1 g of the product (2.4 mmol) obtained from step III-1 was dissolved in 20 mL of THF to form a solution. 0.84 mL of Et$_3$N (6.02 mmol) and 0.03 g of DMAP (0.24 mmol) were added to the solution under an ice bath (the solution temperature was lower than 5° C.). 1.29 g of acyl chloride (3.6 mmol) was slowly added to the solution. During this step, the solution was slightly exothermic and a white precipitate was formed. After the solution temperature returned to room temperature, the solution was stirred for about 1 hour. 20 mL of an HCl aqueous solution (5%) was added to the solution under an ice bath. The solution was extracted using 20 ml of ethylacetate. An organic phase was collected, dried through sodium sulfate and filtered. After removal of solvent from a filtrate by low-pressure condensation, a column chromatography was performed using n-hexane and ethyl acetate (EA) as an eluting solution. A white solid was obtained, with 76% yield.

Example 4

Preparation of the Liquid Crystal Compound IV

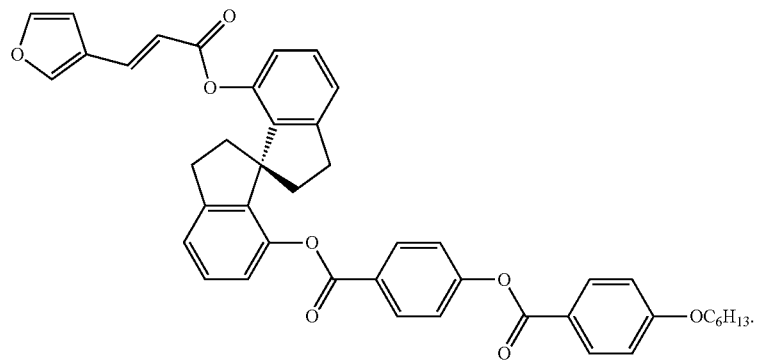

Step IV-1:
Synthesis Scheme:

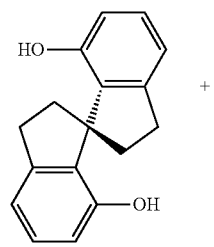

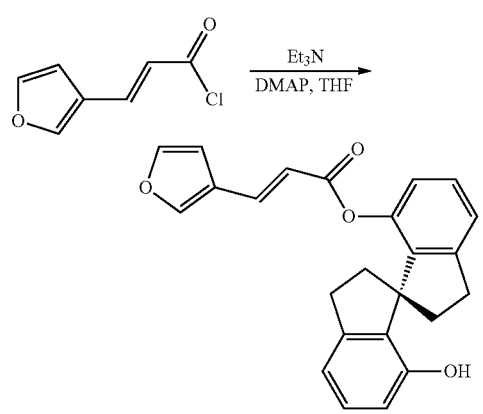

1 g of the product (chiral diol) ((S)-3) (3.96 mmol) obtained from step 1-7 was dissolved in 10 mL of THF to form a solution. 1.4 mL of Et₃N (10.04 mmol) and 0.05 g of DMAP (0.4 mmol) were added to the solution under an ice bath (the solution temperature was lower than 5° C.). 0.62 g of acyl chloride (3.96 mmol) was slowly added to the solution. During this step, the solution was slightly exothermic and a white precipitate was formed. After the solution temperature returned to room temperature, the solution was stirred for about 1 hour. 20 mL of an HCl aqueous solution (5%) was added to the solution under an ice bath. The solution was extracted using 20 ml of ethyl acetate. An organic phase was collected, dried through sodium sulfate and filtered. After removal of solvent from a filtrate by low-pressure condensation, a column chromatography was performed using n-hexane and ethyl acetate (EA) as an eluting solution. A white solid was obtained, with 66% yield.

Step IV-2:
Synthesis Scheme:

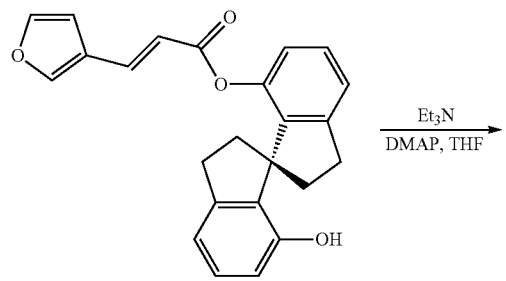

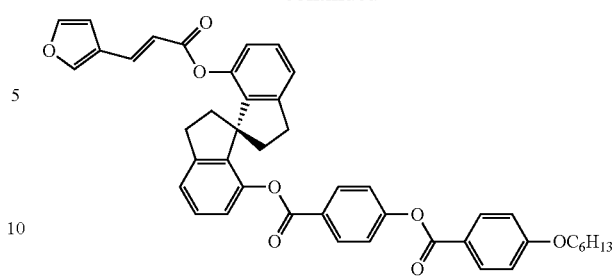

1 g of the product (2.4 mmol) obtained from step IV-1 was dissolved in 20 mL of THF to form a solution. 0.84 mL of Et₃N (6.02 mmol) and 0.03 g of DMAP (0.24 mmol) were added to the solution under an ice bath (the solution temperature was lower than 5° C.). 1.29 g of acyl chloride (3.6 mmol) was slowly added to the solution. During this step, the solution was slightly exothermic and a white precipitate was formed. After the solution temperature returned to room temperature, the solution was stirred for about 1 hour. 20 mL of an HCl aqueous solution (5%) was added to the solution under an ice bath. The solution was extracted using 20 ml of ethyl acetate. An organic phase was collected, dried through sodium sulfate and filtered. After removal of solvent from a filtrate by low-pressure condensation, a column chromatography was performed using n-hexane and ethyl acetate (EA) as an eluting solution. A white solid was obtained, with 79% yield.

Example 5

HTP Values of the Liquid Crystal Compounds

The HTP values of the present liquid crystal compounds and conventional liquid crystal compounds are compared and shown in Table 1.

TABLE 1

| | Conventional liquid crystal compound Ia | Conventional liquid crystal compound IIa | The present liquid crystal compound I | The present liquid crystal compound II |
|---|---|---|---|---|
| HTP ($\mu m^{-1}$) | 44 | 57 | 60 | 59 |

Conventional liquid crystal compound Ia:

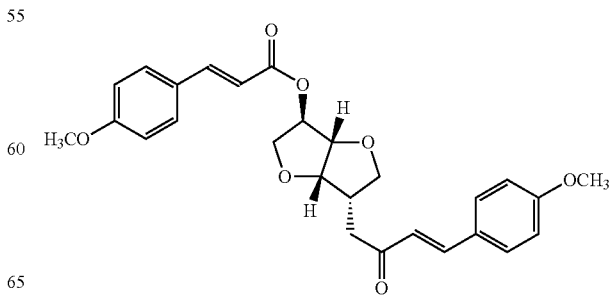

Conventional liquid crystal compound IIa:

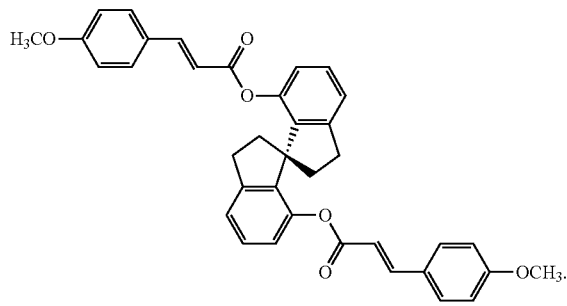

In accordance with Table 1, the results indicate that the HTP values of the present liquid crystal compounds are larger than those of the conventional liquid crystal compounds.

Example 6

Temperature Dependence of the Liquid Crystal Compounds

The temperature dependence of the present liquid crystal compounds and conventional liquid crystal compounds are compared and shown in Table 2.

Experiment conditions: wavelength: 580 nm, measurement temperature: 0-50° C.

TABLE 2

| | Conventional liquid crystal compound Ia | Conventional liquid crystal compound IIa | The present liquid crystal compound I | The present liquid crystal compound II |
|---|---|---|---|---|
| $d\lambda/dT$ | −0.74 | −0.63 | −0.26 | −0.33 |

In accordance with Table 2, the results indicate that the temperature dependence ($d\lambda/dT$) of the present liquid crystal compounds is more stable than that of the conventional liquid crystal compounds, making the present liquid crystal compounds suitable for application in cholesteric liquid crystal displays.

Example 7

Relationship Between Illumination Time and Alteration in Wavelength for the Liquid Crystal Compounds The relationships between illumination time and alteration in wavelength for the present liquid crystal compounds and conventional liquid crystal compounds are compared and shown in Table 3.

Experiment conditions: wavelength: 365 nm, power: 4 mW/cm$^2$

TABLE 3

| | Blue (450 nm) | Green (550 nm) | Red (650 nm) | Rate of alteration in wavelength (blue→green) (nm/sec) | Rate of alteration in wavelength (green→red) (nm/sec) |
|---|---|---|---|---|---|
| Conventional liquid crystal compound Ia | 0 min | 1 min | 4 min | 1.67 | 0.56 |
| Conventional liquid crystal compound IIa | 0 min | 4 min | 2 hr 20 min | 0.42 | 0.012 |
| The present liquid crystal compound I | 0 min | 3 hr 20 min | 8 hr 20 min | 0.0083 | 0.0056 |
| The present liquid crystal compound II | 0 min | 2 hr 20 min | 7 hr 50 min | 0.0119 | 0.0051 |

In accordance with Table 3, the results indicate that the rate (nm/sec) of alteration in wavelength of the present liquid crystal compounds is significantly slower than that of the conventional liquid crystal compounds under the same illumination condition, capable of precise control to color wavelengths of cholesteric liquid crystal, making the present liquid crystal compounds suitable for application in cholesteric liquid crystal displays. Additionally, in accordance with such property, the present liquid crystal compounds can also be applied as an indicator for detecting UV light.

Example 8

Color Stability of the Liquid Crystal Compounds

The optical stability of the present liquid crystal compounds and conventional liquid crystal compounds are compared and shown in Table 4.

Experiment conditions: wavelength: 365 nm, power: 1 μW/cm$^2$ (indoor fluorescent light)

TABLE 4

| | Blue (450→460 nm) | Green (550→560 nm) | Red (630→640 nm) |
|---|---|---|---|
| Conventional liquid crystal compound Ia | 0.2 min | 0.2 min | 0.2 min |
| Conventional liquid crystal compound IIa | 0.2 min | 6 min | 12 min |
| The present liquid crystal compound I | 0.5 min | 30 min | 30 min |
| The present liquid crystal compound II | 0.5 min | 30 min | 30 min |

In accordance with Table 4, the results indicate that the blue, green and red colors of the present liquid crystal compounds are more stable than those of the conventional liquid crystal compounds under the same surrounding environment (conventional indoor fluorescent light).

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A liquid crystal compound of Formula (I):

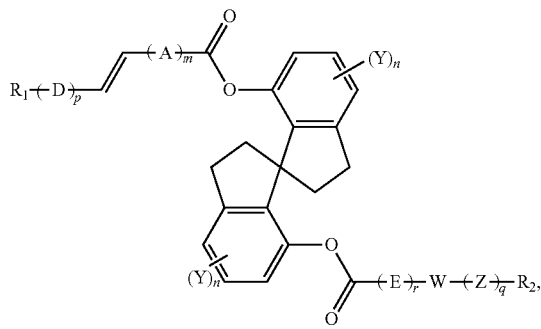

(I)

wherein
A is benzene, naphthalene, pyridine, furan, thiophene or a single bond;
D is benzene, naphthalene, pyridine, furan, thiophene or a single bond;
$R_1$ and $R_2$ are C1-10 alkyl, C1-10 alkoxy, fluoro or trifluoro methyl;
E is benzene, naphthalene, pyridine, furan, thiophene or a single bond;
W is —CO—O—, —O—CO—, —O—, —$CH_2$—$CH_2$—, —$CH_2$—O— or a single bond;
Z is benzene, naphthalene, pyridine, furan, thiophene or a single bond;
Y is hydrogen, methyl, ethyl or propyl;
m is 0, 1 or 2;
p is 0, 1 or 2;
r is 0, 1 or 2;
q is 0, 1 or 2; and
n is 0, 1, 2 or 3.

2. The liquid crystal compound as claimed in claim 1, wherein the liquid crystal compound comprises

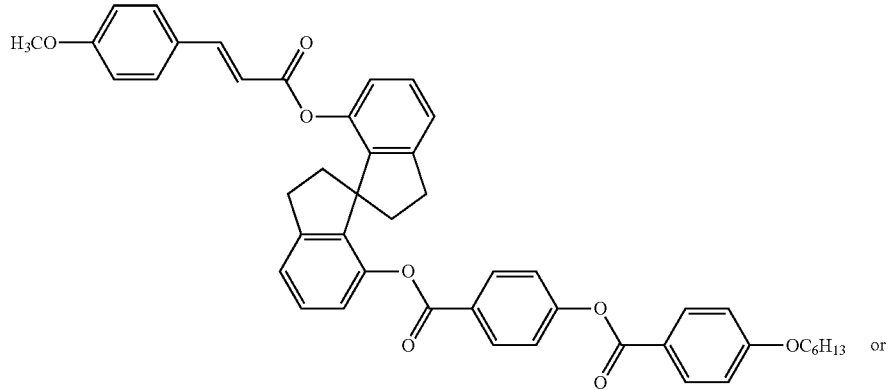

or

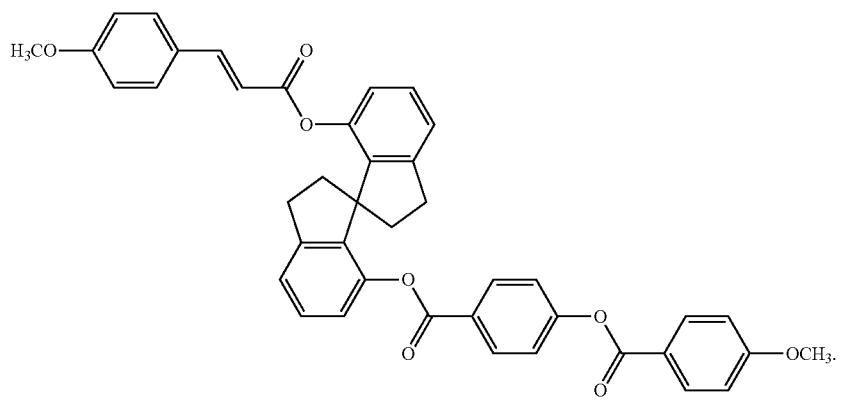

3. A liquid crystal display, comprising:
an upper substrate;
a lower substrate opposed to the upper substrate; and
a liquid crystal layer disposed between the upper substrate and the lower substrate, wherein the liquid crystal layer comprises the liquid crystal compound as claimed in claim 1.

4. A photochromic material, comprising:
a substrate; and
a micro-cell liquid crystal layer coated on the substrate, wherein the micro-cell liquid crystal layer comprises the liquid crystal compound as claimed in claim 1.

5. A liquid crystal compound of Formula:

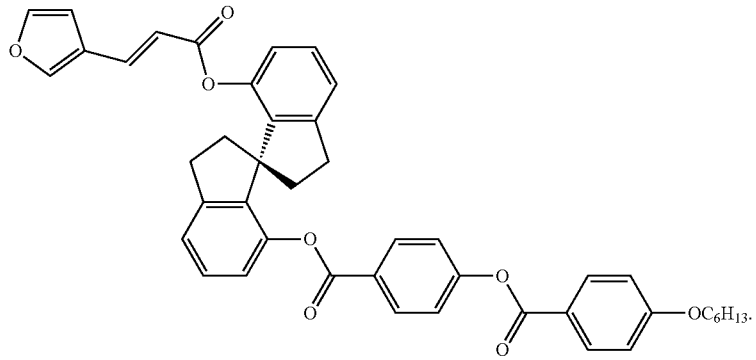

* * * * *